US012584794B2

(12) United States Patent
Kim et al.

(10) Patent No.: US 12,584,794 B2
(45) Date of Patent: Mar. 24, 2026

(54) METHOD FOR QUANTITATIVELY ANALYZING FLUORESCENT DYES LABELED ON EXTRACELLULAR VESICLE BY USING FLUORESCENCE CORRELATION SPECTROSCOPY, AND USE THEREOF

(71) Applicants: THE ASAN FOUNDATION, Seoul (KR); UNIVERSITY OF ULSAN FOUNDATION FOR INDUSTRY COOPERATION, Ulsan (KR)

(72) Inventors: Sang Yeob Kim, Seoul (KR); Chan Gi Pack, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 143 days.

(21) Appl. No.: 18/557,769

(22) PCT Filed: Apr. 28, 2022

(86) PCT No.: PCT/KR2022/006072
§ 371 (c)(1),
(2) Date: Oct. 27, 2023

(87) PCT Pub. No.: WO2022/231334
PCT Pub. Date: Nov. 3, 2022

(65) Prior Publication Data
US 2024/0369412 A1     Nov. 7, 2024

(30) Foreign Application Priority Data
Apr. 29, 2021     (KR) ........................ 10-2021-0055917

(51) Int. Cl.
*G01J 3/457*          (2006.01)
*G01J 3/44*           (2006.01)
(Continued)

(52) U.S. Cl.
CPC ................. *G01J 3/457* (2013.01); *G01J 3/44* (2013.01); *G01N 21/6408* (2013.01);
(Continued)

(58) Field of Classification Search
CPC ........ G01J 3/457; G01J 3/44; G01N 21/6408; G01N 21/6428; G01N 21/6458;
(Continued)

(56) References Cited

U.S. PATENT DOCUMENTS

2005/0191705 A1* 9/2005 Werner ................ G01N 33/582
                                                            435/7.1
2007/0215815 A1* 9/2007 Wohland .............. G01N 33/582
                                                            250/458.1
(Continued)

FOREIGN PATENT DOCUMENTS

JP      2021-509013 A      3/2021
KR  10-2018-0078173 A      7/2018
(Continued)

OTHER PUBLICATIONS

Corso et al. "Systematic characterization of extracellular vesicle sorting domains and quantification at the single molecule-single vesicle level by fluorescence correlation spectroscopy and single particle imaging", Journal of Extracellular Vesicles vol. 8, 11663043. doi:10.1080/20013078.2019.1663043 (Year: 2019).*
(Continued)

*Primary Examiner* — Dominic J Bologna
*Assistant Examiner* — Akbar H. Rizvi
(74) *Attorney, Agent, or Firm* — Oblon, McClelland, Maier & Neustadt, L.L.P.

(57) ABSTRACT
A method of quantifying fluorescent dyes labeled on extracellular vesicles, including providing an extracellular vesicle molecule labeled with a fluorescence dye molecule, and determining a brightness of each of the extracellular vesicle
(Continued)

molecule labeled with the fluorescence dye molecule and the fluorescence dye molecule through fluorescence correlation spectroscopy (FCS) of the extracellular vesicle molecule and the fluorescence dye molecule.

12 Claims, 3 Drawing Sheets

(51) Int. Cl.
| | | |
|---|---|---|
| *G01N 21/64* | (2006.01) | |
| *G01N 33/58* | (2006.01) | |
| *G01N 33/68* | (2006.01) | |

(52) U.S. Cl.
CPC ..... *G01N 21/6428* (2013.01); *G01N 21/6458* (2013.01); *G01N 33/582* (2013.01); *G01N 33/68* (2013.01); *G01N 2021/6441* (2013.01)

(58) Field of Classification Search
CPC ................. G01N 33/582; G01N 33/68; G01N 2021/6441; G01N 2500/20
See application file for complete search history.

(56) References Cited

U.S. PATENT DOCUMENTS

| | | | | |
|---|---|---|---|---|
| 2009/0040518 | A1* | 2/2009 | Widengren | ........ G01N 21/6408 356/317 |
| 2018/0273759 | A1 | 9/2018 | Patton et al. | |
| 2020/0148746 | A1* | 5/2020 | Koh | ..................... A61K 31/519 |
| 2020/0191778 | A1* | 6/2020 | Huang | ................. G01N 33/588 |

FOREIGN PATENT DOCUMENTS

| | | | | | |
|---|---|---|---|---|---|
| KR | 10-2019-0083237 | A | | 7/2019 | |
| KR | 10-2020-0027330 | A | | 3/2020 | |
| KR | 20200027330 | A | * | 3/2020 | ......... G01N 21/6445 |

OTHER PUBLICATIONS

Fu et al. "High-throughput fluorescence correlation spectroscopy enables analysis of surface components of cell-derived vesicles", Analytical and Bioanalytical Chemistry vol. 412, 11 (2020): 2589-2597, doi:10.1007/s00216-020-02485-z (Year: 2020).*

Snell et al. "Cell-Derived Vesicles for in Vitro and in Vivo Targeted Therapeutic Delivery", ACS Omega vol. 4,7 12657-12664. Jul. 24, 2019, doi:10.1021/acsomega.9b01353 (Year: 2019).*

International Search Report mailed on Jul. 20, 2022 in PCT/KR2022/006072 filed on Apr. 28, 2022 (9 pages).

Corso et al. "Systematic characterization of extracellular vesicle sorting domains and quantification at the single molecule-single vesicle level by fluorescence correlation spectroscopy and single particle imaging", Journal of extracellular vesicles, 2019, vol. 8, No. 1663043, 24 pages.

Maria Isabel González et al., Covalently Labeled Fluorescent Exosomes for In Vitro and In Vivo Applications, biomedicines 2021, 9, 81. https://doi.org/10.3390/biomedicines9010081 (16 pages).

Pascal Tanner et al., Enzymatic Cascade Reactions inside Polymeric Nanocontainers: A Means to Combat Oxidative Stress, Chemistry A European Journal, 2011,17, 4552-4560 (9 pages).

* cited by examiner

CPM IN CPM/DYE OF SAMPLE = NUMBER OF DYES
BOUND TO ONE EXOSOME

METHOD FOR QUANTITATIVELY ANALYZING FLUORESCENT DYES LABELED ON EXTRACELLULAR VESICLE BY USING FLUORESCENCE CORRELATION SPECTROSCOPY, AND USE THEREOF

CROSS REFERENCE TO RELATED APPLICATIONS

This application is a National Stage entry under 35 U.S.C. § 371 of PCT/KR2022/006072, filed on Apr. 28, 2022, and claims priority to Korean Patent Application No. 10-2021-0055917, filed on Apr. 29, 2021. The entire contents of both are incorporated herein by reference.

TECHNICAL FIELD

The present disclosure relates to a method of quantitatively analyzing fluorescence dyes labeled on extracellular vesicles by using fluorescence correlation spectroscopy, and use thereof.

BACKGROUND ART

Extracellular vesicles include exosomes, microvesicles, and the like, and among these, exosomes, which have been extensively researched and developed, are attracting much attention as a next-generation therapeutic agent. Exosomes, which have a diameter of 30 nm to 200 nm, are much smaller than cells having a size of 10,000 nm to 20,000 nm, and thus can be administered via various routes without the risk of embolism, which is a potential risk factor for cell therapeutic agents. In addition, unlike cells, exosomes have the advantages of a very low risk of tumor formation due to being unable to self-replicate, being expected to have a relatively long shelf life, and being released as products after various quality controls.

However, in the case of systemic administration such as intravenous injection, nano-sized extracellular vesicles reach not only a target organ but also various other organs and can be absorbed into tissues and cells. Thus, to develop extracellular vesicles as a therapeutic agent, evaluation of the biodistribution experiment of extracellular vesicles in consideration of administration route is essentially required.

The biodistribution experiment of extracellular vesicles by using optical imaging is a technique used by many researchers since fluorescent substances can be easily labeled and observed through images. However, the method using a cell tracker, which is used by many researchers, has the advantage of simple and convenient manipulation since the cell membrane is stained through integration of a fluorescence dye, but has problems such as diffusion or escape of the dye or an increase in the size of extracellular vesicles. Recently, a method of covalently bonding a fluorescent substance to an amine or thiol group of a cell membrane protein, or a method for copper-free click chemistry labeling of a fluorescent substance linked to a dibenzocyclooctyne (DBCO) group by using Ac4ManNAz or Kdo-N3 is used, and these methods enable accurate image observation since a fluorescence dye does not escape even after long-term imaging.

Meanwhile, to evaluate the accurate biodistribution experiment of extracellular vesicles by using such optical imaging, it is an important factor to measure the labeling efficiency of various fluorescence dyes. However, since there is no method of quantifying the number of fluorescence dyes labeled on one extracellular vesicle, it is difficult to accurately measure the labeling efficiency of fluorescence dyes.

Therefore, as a result of having studied a method for measuring the efficiency of fluorescence dyes for labeling extracellular vesicles, the inventors of the present disclosure confirmed that, when fluorescence correlation spectroscopy (FCS) is used, the number of labeled fluorescence dyes per extracellular vesicle can be quantified, thus completing the present disclosure.

DISCLOSURE

Technical Problem

An object of the present disclosure is to provide a method of quantifying fluorescence dyes labeled on extracellular vesicles.

Another object of the present disclosure is to provide a method of quantifying extracellular vesicles by using the method.

Still another object of the present disclosure is to provide a method of evaluating a therapeutic candidate material by using the method.

Still another object of the present disclosure is to provide a method of detecting a target protein in vivo by using the method.

Still another object of the present disclosure is to provide a kit for detecting a target protein in vivo by using the method.

Technical Solution

To achieve the above object, an aspect provides a method of quantifying fluorescence dyes labeled on extracellular vesicles, including the steps of: providing an extracellular vesicle molecule labeled with a fluorescence dye; and performing fluorescence correlation spectroscopy (FCS) of the extracellular vesicle molecule labeled with a fluorescence dye and a fluorescence dye molecule to determine the brightness of each molecule.

The term "fluorescence correlation spectroscopy (FCS)" refers to measurement of the Brownian motion or free diffusion method of a fluorescently labeled target molecule in a medium by a laser confocal microscope system, and refers to an analytical technique for quantitatively obtaining the diffusion coefficient (size) of a target molecule, the number of average particles in an observation volume, intermolecular interactions, and the like by detecting fluctuations in fluorescence intensity over time and calculating a fluorescence auto-correlation function.

FCS is an analytical fluorescence technique consisting of a confocal optical system (objective lens at a high magnification and a high aperture), a laser light source, a high-sensitivity and high-speed detector, a correlator that calculates the fluorescence auto-correlation function, and software that performs mathematical model fitting (curve fitting) of the fluorescence auto-correlation function with a theoretical model formula, and the fluorescence auto-correlation function obtained through measurement may obtain various physical parameters (molecular size, number of average particles, fluorescence brightness per molecule, dissociation constant, and the like) mentioned above by using a plurality of mathematical models.

Currently, FCS has been developed in a form combined with a high-resolution confocal microscope, and is the only way to detect in real time the absolute concentration, physical size (diffusion coefficient), fluorescent brightness per molecule (fluorescence efficiency), and the presence or absence of intermolecular interaction, for fluorescent molecules present in cells through high-resolution cell imaging by a confocal microscope, as well as for solution samples.

When FCS is used in the detection and measurement of extracellular vesicle and the like contained in a biological sample, the concentration or intermolecular interaction of fluorescently labeled target molecules contained in a solution may be monitored in almost real time without undergoing a physical separation process. Therefore, a detection system using FCS may avoid a complicated Bound/Free separation process required for conventional analysis means, e.g., ELISA that have been mainly used in biomolecule detection systems. Thus, this technique can measure large amounts of samples with high sensitivity within a short time, and is also suitable for automated measurements.

The term "extracellular vesicle" refer to nanoparticles naturally secreted by living cells in a state of being encapsulated in the lipid bilayer, and is a concept of including exosomes and microvesicles. This refers to a particle that is unable to replicate due to not containing a functional nucleus. Extracellular vesicles are important mediators for intercellular signal transduction in unicellular organisms as well as in multicellular organisms, and have been found to play an important role in signal transduction between species. Extracellular vesicles, which are made to deliver various physiologically active substances such as genetic materials or proteins to other cells evolutionarily, are rapidly and industrially applied not only to basic biological research, but also to development of therapeutic agents, development as therapeutic delivery systems, and liquid biopsy.

The brightness of each molecule means fluorescent brightness, is expressed in units of kHz in fluorescence correlation spectroscopy, and may be an absolute value of a specific molecule.

The term "fluorescent brightness" refers to the brightness of fluorescence emitted by excitation of a phosphor, and is also referred to as fluorescence intensity.

The method may include determining the number of labeled fluorescence dye molecules per extracellular vesicle by determining a brightness value of fluorescence dye molecules with respect to the brightness of fluorescence dye-labeled extracellular vehicle molecules.

Specifically, the number of labeled fluorescent dye molecules per extracellular vesicle may be determined by dividing the measured averaged fluorescence intensity value of extracellular vesicle molecules by an averaged fluorescence intensity value of fluorescence dye molecules.

Averaged fluorescence intensity refers to an average value of the intensities of fluorescence emitted by multiple molecules, and the averaged fluorescence intensity of one molecule may be calculated by dividing the fluorescence intensity of a sample containing multiple molecules by the number of detected molecules.

The number of labeled fluorescent dye molecules per extracellular vesicle is an integer, and if not an integer, the number may be determined as an integer rounded from the nearest tenth.

In an embodiment, the number of fluorescence dyes bound to one exosome molecule may be calculated by dividing an averaged fluorescent brightness value of one exosome molecule labeled with fluorescence dyes, as measured by fluorescence correlation spectroscopy of a sample in which quantified exosomes are labeled with fluorescence dyes, by an averaged fluorescent brightness value of one fluorescence dye molecule.

The extracellular vesicles labeled with fluorescent dyes may be extracellular vesicle molecules labeled with a plurality of fluorescent dyes having different brightness values.

The method may include deriving a correlation function by determining the brightness of molecules having different conditional variables.

The conditional variables may be selected from the group consisting of factors that may affect the size or number of extracellular vesicles, the concentration of fluorescent dyes used to treat extracellular vesicles, and labeling of fluorescence dyes on extracellular vesicles.

The extracellular vesicle molecule labeled with fluorescent dyes may be one chemically labeled with fluorescent dyes.

The term "fluorescence dye" refers to a material that generates light by chemical treatment or changes in physical conditions.

The fluorescent dye may be, but is not limited to, any one selected from the group consisting of fluorescein, fluorescein chlorotriazinyl, fluorescein isothiocyanate (FITC), rhodamine green, rhodamine red, tetramethylrhodamine, Oregon green, Alexa Fluor, JOE, ROX, HEX, Texas Red, TET, TRITC, TAMRA, cyanine-based dyes, and thiadicarbocyanine dyes.

In addition, the dye may be, but is not limited to, any one reactive derivative selected from the group consisting of N-hydroxysuccinimide ester (NHS ester), isothiocyanates, carboxylic acids, and sulfonyl chlorides.

The fluorescence correlation spectroscopy may include the steps of: deriving a fluorescence auto-correlation function by irradiating a sample containing extracellular vesicle molecules labeled with fluorescent dyes, with an excitation laser, and then measuring a generated fluorescence signal with a detector; analyzing the fluorescence auto-correlation function; and calculating the fluorescent brightness of one extracellular vesicle molecule by using the fluorescent brightness of the sample and the number of extracellular vesicle molecules contained in the sample.

The fluorescent brightness of one molecule is expressed in units of cpm, and cpm is an abbreviation of count rate per molecule and refers to the averaged intensity of fluorescence emitted by one molecule.

In an embodiment, the fluorescence intensity (CPM) of one extracellular vesicle molecule may be calculated through the steps of: setting a solution sample containing extracellular vesicle molecules labeled with fluorescence dyes in an FCS device, and then measuring a fluorescence signal generated through irradiation of an excitation laser by using a detector, to thereby derive a fluorescence auto-correlation function; and fitting (curve fitting) the derived fluorescence auto-correlation function with a mathematical theoretical model formula.

The extracellular vesicle molecule may be any one selected from the group consisting of an exosome, a microvesicle, an intraluminal vesicle, a multivesicular body, a multivesicular endosome, and a vesicle isolated from an endosome or the plasma membrane.

The term "exosome" refers to an intraluminal vesicle (ILV) released into the extracellular space as a result of fusion of a multivesicular body (MVB) with the cell membrane, after an early endosome is formed through primary invasination of the cell membrane, and the MVB containing the ILV is formed through secondary invasination of the endosome membrane. The size of exosomes is known to be approximately 30 nm to 200 nm in diameter, and although there are slight differences depending on the type of cells of origin, the exosome membrane contains surface proteins (surface markers) such as CD9, CD63, and CD81, and it is known that exosomes contain proteins such as TSG101 and ALIX, which can be proven to originate from endosomes. In addition, exosomes contain proteins, including growth factors, cytokines and the like which have various functions, and nucleic acids such as mRNA and miRNA, and have components and efficacy that reflect the characteristics of cells of origin. In particular, stem cell exosomes are known to have the effects of regulating the differentiation of stem cells, promoting regeneration and growth, and inducing specific immune responses, and thus, the development of therapeutic agents using the same is actively ongoing.

The term "microvesicle" refers to a particle shed from the cell membrane after outward budding of the cell membrane. The size of microvesicles is known to be 100 nm to 1,000 nm, and relatively little is known about microvesicles compared to exosomes.

Another aspect provides a method of quantifying extracellular vesicles, including a step of quantifying extracellular vesicle molecules in an unidentified sample by inputting a brightness value of the extracellular vesicle molecules labeled with fluorescence dyes in the unidentified sample, into the correlation function for the brightness value of extracellular vesicle molecules labeled with a plurality of groups of fluorescence dyes at specific concentrations, as previously determined through the method of quantifying fluorescence dyes labeled on extracellular vesicles.

Another aspect provides a method of evaluating a therapeutic candidate material, including a step of evaluating extracellular vesicles that are treated or administered in vitro or in vivo and including a candidate material or extracellular vesicles as a candidate material by using the method of quantifying fluorescence dyes labeled on extracellular vesicles.

It has been reported that stem cell-derived exosomes or HEK293T cell-derived exosomes do not induce toxicity in in-vitro and in-vivo tests. In particular, it has been reported that human stem cell-derived exosomes do not contain co-stimulatory molecules such as MHC Class I (or HLA Class I), Class II (or HLA Class II), or CD80 and CD86, which can induce immune responses. Thus, it is expected that human stem cell-derived exosomes will not cause immune rejection when developed as a therapeutic agent. It has also been reported that no particular immunotoxicity is induced even when human stem cell-derived exosomes are repeatedly administered to mice for a long period of time. However, in the case of systemic administration such as intravenous injection, nano-sized extracellular vesicles reach not only a target organ but also various organs and can be absorbed into tissues and cells. Thus, to develop extracellular vesicles as a therapeutic agent, evaluation of the biodistribution experiment of extracellular vesicles in consideration of administration route is required.

According to an embodiment, when the number of labeled fluorescence dyes per extracellular vesicle is quantified, the proportion of administered extracellular vesicles labeled with fluorescence dyes that have reached a target organ and what proportion of the extracellular vesicles reaches various organs can be accurately evaluated through measurement of fluorescence distribution and fluorescence intensity in vivo.

Another aspect provides a method of detecting a target protein in vivo, including the steps of: providing extracellular vesicle molecules that are isolated from a cell line expressing a protein that specifically binds to the target protein, and are labeled with fluorescence dyes; quantifying the number of fluorescence dyes labeled on one extracellular vesicle molecule according to the concentration of treated fluorescence dyes measured through fluorescence correlation spectroscopy of the extracellular vesicle molecules labeled with fluorescence dyes; and allowing an isolated biological sample containing the target protein to bind to the quantified extracellular vesicle molecules in which the number of labeled fluorescence dyes is adjusted, and then detecting fluorescence.

Another aspect provides a kit for detecting a target protein in vivo, including extracellular vesicle molecules that are isolated from a cell line expressing a target protein or a protein that binds to the target protein, and are labeled with fluorescence dyes, wherein the extracellular vesicle molecules labeled with fluorescence dyes have an adjusted number of labeled fluorescence dyes and are quantified, through the method of quantifying fluorescence dyes labeled on extracellular vesicles.

The target protein may be an autoantibody.

The methods and the kit may be used in an autoantibody test. The autoantibody test may be used for diagnosing an autoimmune disease or evaluating the severity thereof, or monitoring the prognosis of an autoimmune disease, such as exacerbation or recurrence or monitoring the therapeutic effect thereof.

By using the methods and the kit, a more accurate autoantibody test may be possible through quantitative evaluation of the presence or absence of an autoantibody in a biological sample (e.g., blood) of an individual and the autoantibody present therein.

The redundant contents are omitted in consideration of complexity of the present specification, and the terms not otherwise defined in the present specification have the meanings commonly used in the technical field to which the present disclosure pertains.

Advantageous Effects

When a method of quantifying fluorescence dyes labeled on extracellular vesicles, according to an embodiment, is used, the number of labeled fluorescence dyes per extracellular vesicle can be quantified, and thus, the labeling efficiency of the fluorescence dyed can be accurately measured.

In addition, extracellular vesicles included in an unidentified sample can be quantified using fluorescence dyes of which the labeling efficiency has been measured, and more accurate biodistribution experimental results can be obtained. Thus, the extracellular vesicles can be used to evaluate a therapeutic candidate material and can also be used in the quantification of a target protein in vivo, and thus can be widely used.

MODE FOR INVENTION

Hereinafter, the present disclosure will be described in more detail with reference to the following examples. However, these examples are provided for illustrative purposes only and are not intended to limit the scope of the present disclosure.

Example 1. Isolation of Exosomes

Therapeutic exosomes were provided by ExoCoBio and used. Specifically, adipose stem cells were cultured in a DMEM medium containing 10% fetal bovine serum (FBS) and 1% penicillin/streptomycin (Thermo Fisher Scientific; Carlsbad, CA). Thereafter, the medium was replaced by a serum-free medium, and a culture medium secreting exosomes was isolated from the adipose stem cells while culturing for 24 hours to 48 hours. Cell debris and other large particles were removed from the isolated culture medium secreting exosomes through centrifugation and 0.22 μm filtration, followed by purification through a 300 kDa or 500 kDa cut-off filter.

Example 2. Quantification of Exosomes

For the quantification of exosomes, NanoSight NS300 (Malvern Instruments, Malvern, United Kingdom) equipped with a 642 nm laser was used for analysis. To analyze diluted exosomes, the camera level was maintained at 14 and 30 videos were taken at 30 frames per second at intervals of 10 seconds. A minimum of 2,000 particles were tracked and analyzed to avoid statistically insignificant peaks in size distribution. Data was analyzed with NTA 3.0 software.

Example 3. Labeling of Exosomes with Fluorescence Dyes and Observation

A solution containing $2\lambda10^9$ exosomes quantified by using the method described in Example 2 was treated with 0.1 mg and 0.05 mg of a N-hydroxysuccinimide ester (NHS ester) fluorescence dye. Generally, when exosomes are labeled with fluorescence dyes, $NaHCO_3$ is added to maintain an alkaline (e.g., pH 8-9) condition to increase the labeling efficiency of the fluorescence dyes. However, to confirm the effect of pH conditions on the efficiency of labeling of a fluorescence dye on exosomes, the following samples including a sample not treated with $NaHCO_3$ were prepared.

TABLE 1

|  | $NaHCO_3$ treated or not | Concentration of fluorescence dye |
|---|---|---|
| Sample 1 | ○ | 0.1 mg |
| Sample 2 | X | 0.1 mg |
| Sample 3 | ○ | 0.05 mg |

Figure 1:
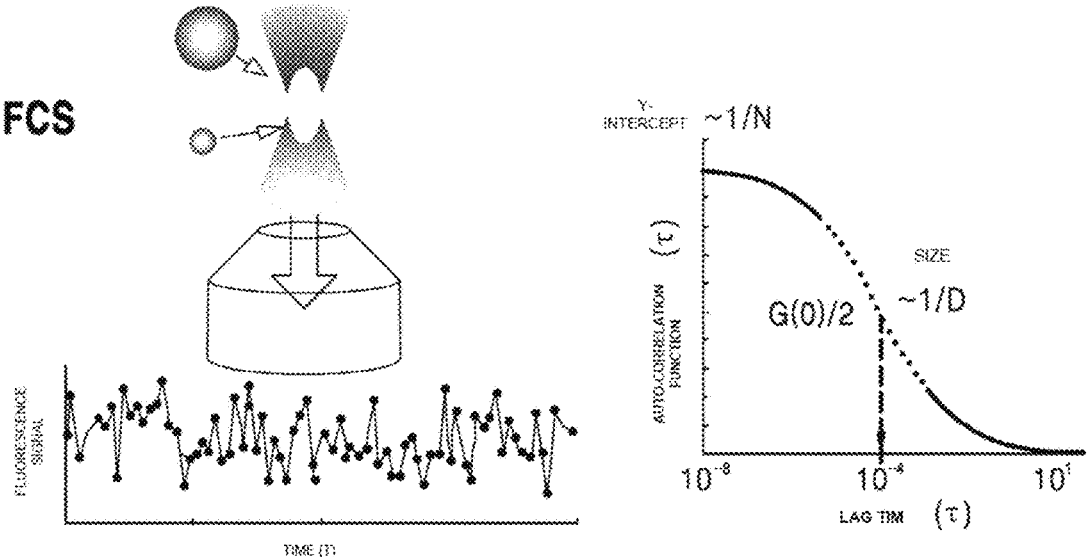
FIG. 1 schematically illustrates a method of analyzing fluorescently labeled exosomes by using fluorescence correlation spectroscopy, according to an embodiment.
Figure 2:
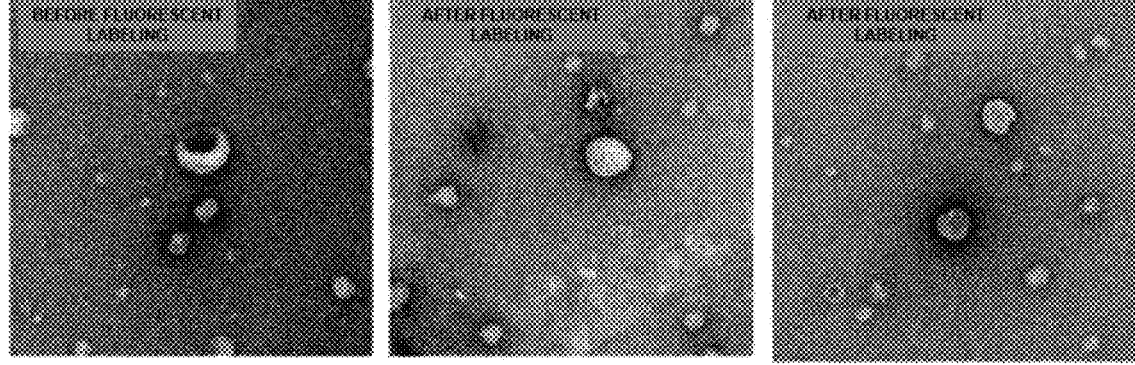
FIG. 2 illustrates the results of observing fluorescence dye-labeled exosomes by a transmission electron microscope, according to an embodiment.

To observe structural changes in fluorescence dye-labeled exosomes, images were acquired using a transmission electron microscope (TEM) (FIG. 2).

Example 4. Analysis of Fluorescence Dye-Labeled Exosomes by Using Fluorescence Correlation Spectroscopy An LSM780 confocal microscope (Carl Zeiss) capable of fluorescence correlation spectroscopy (FCS) and an objective lens (C-Apo 40 X/1.2 NA Water immersion) were selected. 2 μl of each of the fluorescently labeled exosome solutions of Experimental Groups 1 to 4 prepared in Example 3 was placed in an 8-well chambered coverglass (LabTek) exclusive for confocal microscopy, and mounted on an LSM780 stage.

The output of a helium-neon laser (633 nm) was set to 0.2%, and the emission filter band (grating variable type) was adjusted to be 650 nm to 700 nm, and measurement was repeated 10 times or more for 10 seconds with a GaAsp detector.

Figure 3:
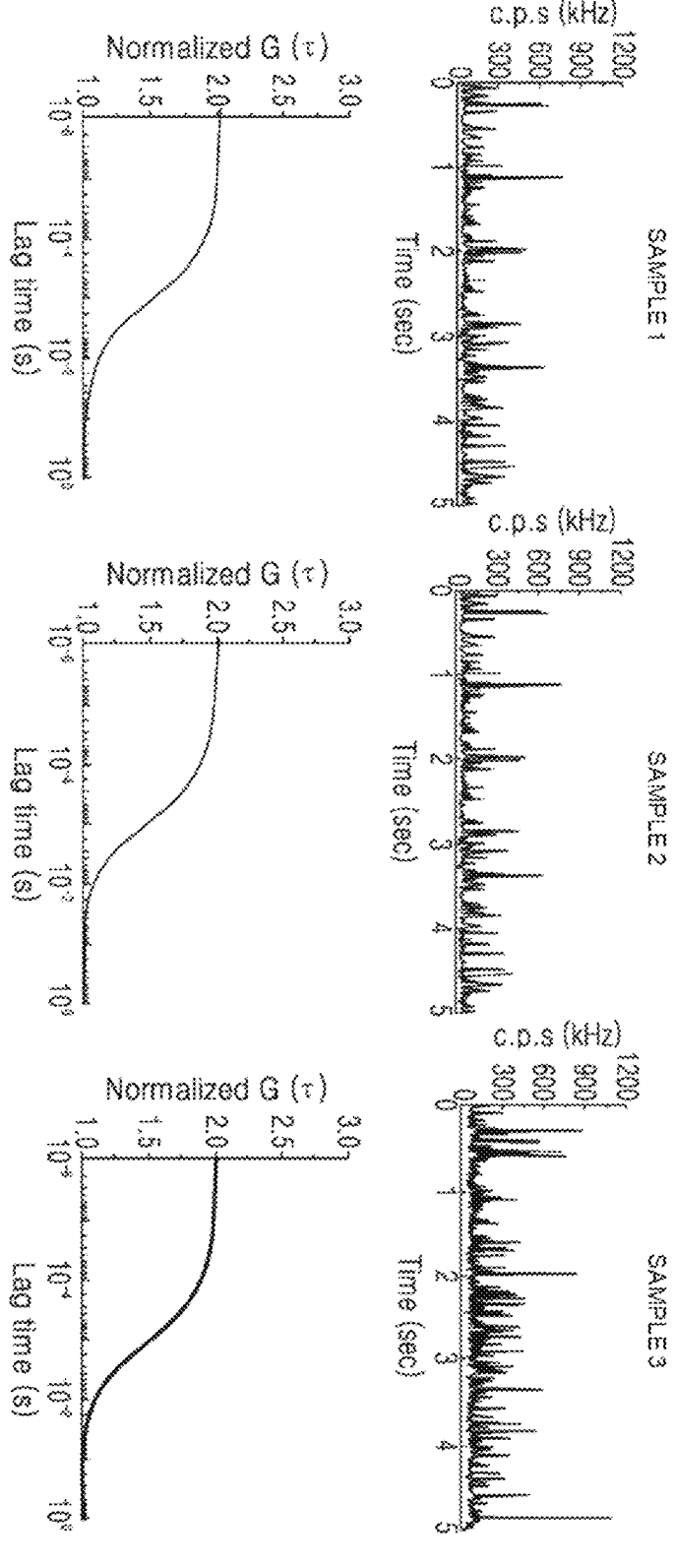
FIG. 3 illustrates the results of measuring the fluorescence intensity and fluorescence auto-correlation function over time of each exosome sample by using fluorescence correlation spectroscopy, according to an embodiment.
Figure 4:
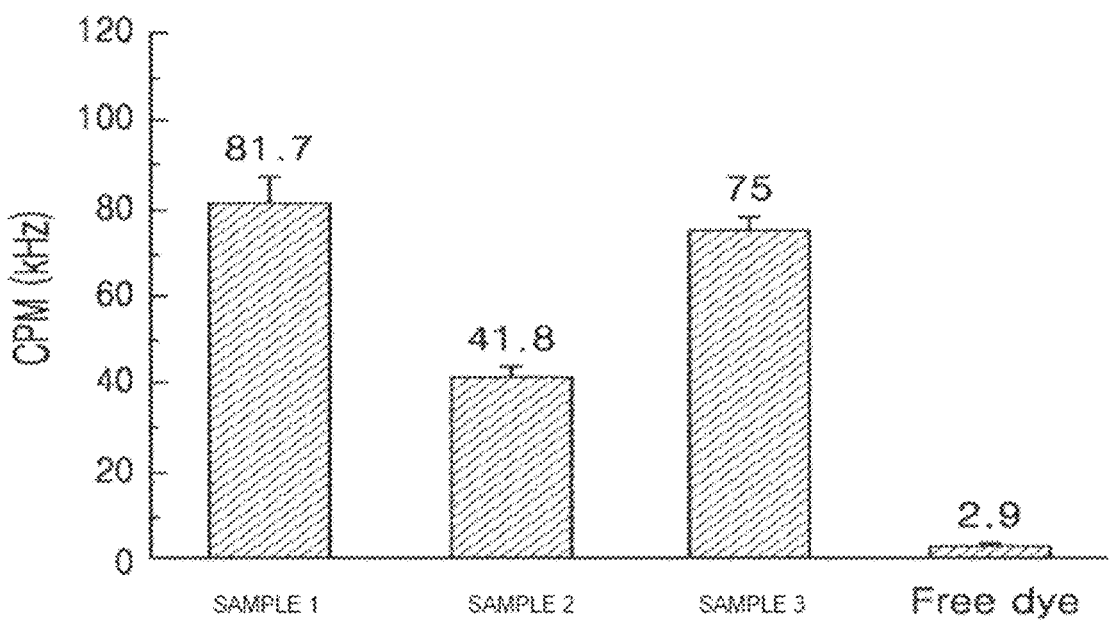
FIG. 4 illustrates the results of calculating the number of fluorescence dyes bound to one exosome in each exosome sample by using fluorescence correlation spectroscopy, according to an embodiment.

A fluorescence auto-correlation function obtained by three measurements was analyzed using a three-dimensional two-component model formula. The fluorescence intensity change and fluorescence auto-correlation function over time of each experimental group are as illustrated in FIG. 3. Through this, the absolute concentrations and relative concentration ratios of stained fluorescent exosomes and free dye were calculated, and the size of stained exosomes and fluorescent brightness per single molecule were measured.

As a result of dividing the measured fluorescent brightness (cpm) value per single exosome by the fluorescent brightness (cpm) value of free dye, the number of fluorescence dyes bound to a single exosome was calculated. The results thereof are as shown in Table 2 (FIG. 3).

TABLE 2

| Number of fluorescence dyes bound to single exosome | |
|---|---|
| Sample 1 | 27 |
| Sample 2 | 14 |
| Sample 3 | 25 |

Through these results, it can be confirmed that the higher the concentration of fluorescence dyes under alkaline conditions, the higher the efficiency of labeling of fluorescence dyes on exosomes.

The invention claimed is:

1. A method of quantifying fluorescent dyes labeled on extracellular vesicles, the method comprising:

providing an extracellular vesicle molecule labeled with a fluorescence dye molecule;

determining a brightness of each of the extracellular vesicle molecule labeled with the fluorescence dye molecule and the fluorescence dye molecule through fluorescence correlation spectroscopy (FCS) of the extracellular vesicle molecule and the fluorescence dye molecule, and determining a number of labeled fluorescence dye molecules per extracellular vesicle by determining a brightness value of the fluorescence dye molecule with respect to the brightness of the extracellular vesicle molecule labeled with a fluorescence dye, wherein the fluorescence correlation spectroscopy comprises:

deriving a fluorescence auto-correlation function by irradiating a sample comprising extracellular vesicle molecules labeled with a fluorescent dye, with an excitation laser, and then measuring a generated fluorescence signal with a detector;

analyzing the fluorescence auto-correlation function; and calculating the fluorescent brightness per extracellular vesicle molecule by using the fluorescent brightness of the sample and the number of extracellular vesicle molecules contained in the sample,

wherein the extracellular vesicle molecule labeled with a
  fluorescence dye is chemically labeled with a fluores-
  cence dye.
2. The method of claim 1, wherein the brightness of each
of the extracellular vesicle molecule labeled with the fluo-
rescence dye molecule and the fluorescence dye molecule is
expressed in units of Hz, and is an absolute value of a
specific molecule.
3. The method of claim 1, wherein the number of labeled
fluorescence dye molecules per extracellular vesicle is an
integer, and the determining comprises determining an inte-
ger rounded to a first decimal place if not an integer.
4. The method of claim 1, wherein the extracellular
vesicle molecule is labeled with a plurality of fluorescence
dye molecules having different brightness values.
5. The method of claim 1, further comprising deriving a
correlation function by determining a brightness of mol-
ecules having different conditional variables.
6. The method of claim 5, wherein the different condi-
tional variables are selected from the group consisting of
factors capable of affecting a size or number of extracellular
vesicle molecules, a concentration of the fluorescence dye
molecule used to treat the extracellular vesicle molecule, and
labeling of the fluorescence dye molecule on the extracel-
lular vesicle molecule.
7. The method of claim 1, wherein the fluorescence dye
molecule is selected from the group consisting of fluores-
cein, fluorescein chlorotriazinyl, fluorescein isothiocyanate
(FITC), rhodamine green, rhodamine red, tetramethylrhod-
amine, Oregon green, Alexa Fluor, JOE, ROX, HEX, Texas
Red, TET, TRITC, TAMRA, cyanine-based dyes, and thi-
adicarbocyanine dyes.
8. The method of claim 1, wherein the fluorescence dye
molecule is at least one reactive derivative selected from the
group consisting of N-hydroxysuccinimide ester (NHS
ester), isothiocyanates, carboxylic acids, and sulfonyl chlo-
rides.
9. The method of claim 1, wherein the extracellular
vesicle molecule is selected from the group consisting of an
exosome, a microvesicle, an intraluminal vesicle, a multi-
vesicular body, a multivesicular endosome, and a vesicle
isolated from an endosome or a plasma membrane.
10. A method of quantifying extracellular vesicles, the
method comprising:
  inputting a brightness value of extracellular vesicle mol-
    ecules labeled with a fluorescence dye in an unidenti-
    fied sample into a correlation function for a brightness value of the extracellular vesicle molecule labeled with
  the fluorescence dye molecule at specific concentra-
  tions determined through quantifying the fluorescent
  dyes using the method of claim 1, thereby quantifying
  the extracellular vesicle molecules in the unidentified
  sample.
11. A method of evaluating a therapeutic candidate mate-
rial, the method comprising:
  evaluating, by using the method of claim 1, extracellular
    vesicles comprising a candidate material or extracellu-
    lar vesicles being the candidate material, wherein the
    extracellular vesicles are administered in vitro or in
    vivo.
12. A method of detecting a target protein in vivo, the
method comprising:
  providing extracellular vesicle molecules that are isolated
    from a cell line expressing a target protein and a protein
    that binds to the target protein, and are labeled with
    fluorescence dyes;
  quantifying a number of labeled fluorescence dyes per
    extracellular vesicle molecule according to a concen-
    tration of the fluorescence dyes measured through
    fluorescence correlation spectroscopy (FCS) of the
    extracellular vesicle molecules labeled with fluores-
    cence dyes; and
  allowing an isolated biological sample comprising the
    target protein to bind to the extracellular vesicle mol-
    ecules in which the number of the labeled fluorescence
    dyes is quantified and adjusted, and then detecting
    fluorescence,
  wherein the fluorescence correlation spectroscopy com-
    prises:
  deriving a fluorescence auto-correlation function by irra-
    diating a sample comprising extracellular vesicle mol-
    ecules labeled with a fluorescent dye, with an excitation
    laser, and then measuring a generated fluorescence
    signal with a detector;
  analyzing the fluorescence auto-correlation function; and
  calculating the fluorescent brightness per extracellular
    vesicle molecule by using the fluorescent brightness of
    the sample and the number of extracellular vesicle
    molecules contained in the sample,
  wherein the extracellular vesicle molecule labeled with a
    fluorescence dye is chemically labeled with a fluores-
    cence dye.

* * * * *